United States Patent

Hoerauf et al.

(10) Patent No.: US 8,608,667 B2
(45) Date of Patent: Dec. 17, 2013

(54) DEVICE AND METHOD FOR OBTAINING BODY FLUID

(75) Inventors: Christian Hoerauf, Oftersheim (DE); Hans List, Hesseneck-Kailbach (DE); Volker Zimmer, Laumersheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 244 days.

(21) Appl. No.: 12/174,346

(22) Filed: Jul. 16, 2008

(65) Prior Publication Data

US 2009/0024059 A1  Jan. 22, 2009

(30) Foreign Application Priority Data

Jul. 17, 2007 (EP) .................................... 07112625

(51) Int. Cl.
*A61B 5/00* (2006.01)
(52) U.S. Cl.
USPC .......................................... 600/583; 606/181
(58) Field of Classification Search
USPC ............................ 600/583, 584; 606/181, 182
See application file for complete search history.

(56) References Cited

U.S. PATENT DOCUMENTS

| 7,025,774 | B2 | 4/2006 | Freeman et al. | |
|---|---|---|---|---|
| 7,223,276 | B2 | 5/2007 | List et al. | |
| 7,374,544 | B2 * | 5/2008 | Freeman et al. | 600/583 |
| 2003/0054044 | A1 | 3/2003 | Potter et al. | |
| 2003/0083685 | A1 | 5/2003 | Freeman et al. | |
| 2003/0199789 | A1 | 10/2003 | Boecker et al. | |
| 2005/0070819 | A1 * | 3/2005 | Poux et al. | 600/576 |
| 2006/0247555 | A1 * | 11/2006 | Harttig | 600/584 |
| 2008/0287831 | A1 * | 11/2008 | Briggs et al. | 600/583 |

FOREIGN PATENT DOCUMENTS

| DE | 19604156 A1 | 8/1997 |
|---|---|---|
| WO | 2005/107596 A2 | 11/2005 |
| WO | 2007/104445 A2 | 9/2007 |

* cited by examiner

*Primary Examiner* — Max Hindenburg
*Assistant Examiner* — Jonathan M Foreman
(74) *Attorney, Agent, or Firm* — Harness, Dickey

(57) ABSTRACT

A device is disclosed for obtaining body fluid, in particular blood, comprising a lancing element having a tip for puncturing the skin of a body part and an actuator coupled with the lancing element for a forward and backward movement of the lancing element, where the lancing element can be inserted into the skin up to an optionally adjustable puncture position. The actuator is adapted to drive the lancing element forwardly to a penetration speed of at most 0.7 m/s when the lancing element penetrates the skin.

19 Claims, 2 Drawing Sheets

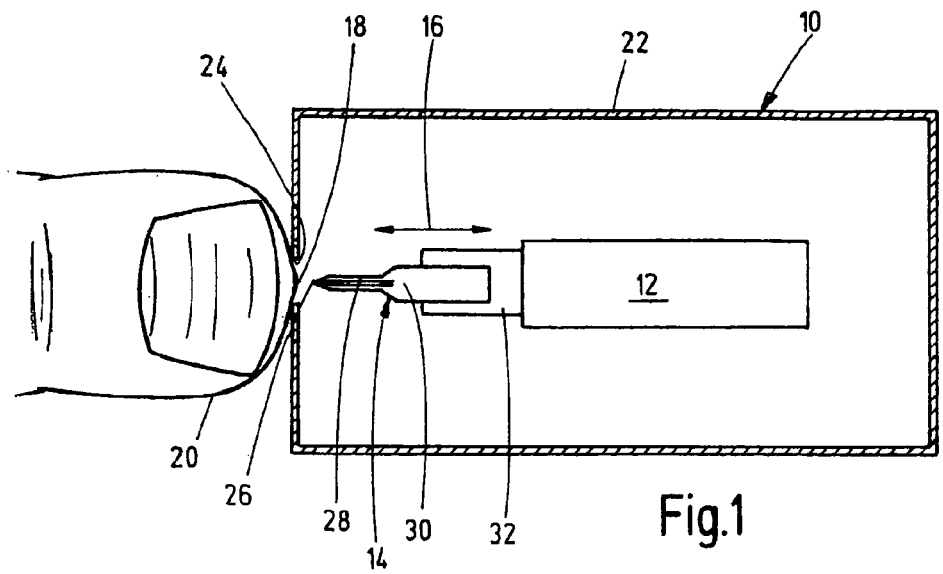
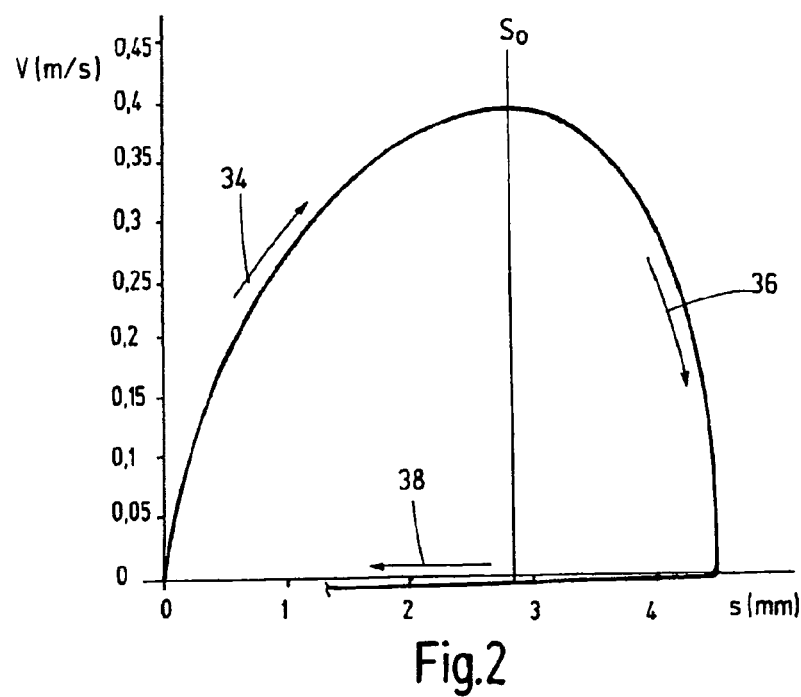

DEVICE AND METHOD FOR OBTAINING BODY FLUID

CROSS-REFERENCE TO RELATED APPLICATIONS

This application claims the benefit and priority of European Patent Application No. 07112625.4, filed Jul. 17, 2007. The entire disclosure of the above application is incorporated herein by reference.

BACKGROUND OF THE INVENTION

1. Field of the Invention

The invention concerns a device for obtaining body fluid, in particular blood, comprising a lancing element having a tip for puncturing the skin of a body part and an actuator coupled with the lancing element for a forward and backward movement of the lancing element, where the lancing element can be inserted into the skin up to an optionally adjustable puncture position. The invention additionally concerns a corresponding method.

2. Description of Related Art

A wide variety of devices are described in the literature which are intended to generate an opening in the skin using a disposable lancet in order to remove a liquid sample and in particular capillary blood in as pain-free a manner as possible. This is an important aspect especially in the case of diabetics for the periodic checks of blood sugar. Also in commercial devices increasingly thinner lancets have been used in the course of time in order to keep the lancing pain as low as possible. In a generic device disclosed in PCT/EP2007/001888 a high speed drive with lancing speeds of 15 m/s is proposed in this connection.

On this basis an object of the invention is to optimize a generic device and a method that can be carried out with this device in the sense of pain reduction where one object of the invention is also to reduce the production complexity. The combination of features stated in the independent claims is proposed to achieve this object. Advantageous embodiments and further developments of the invention are derived from the dependent claims.

BRIEF SUMMARY OF THE INVENTION

It is against the above background that the present invention provides certain unobvious advantages and advancements over the prior art. In particular, the inventors have recognized a need for improvements in a device for obtaining body fluid and in a method for obtaining body fluid.

Although the present invention is not limited to specific advantages or functionality, it is noted that the present invention is based on the finding that surprisingly slow lancing speeds can also be used without them causing an increased pain sensation in the user.

In accordance with one embodiment of the present invention, a device for obtaining body fluid is provided where the device includes a lancing element having a tip for puncturing the skin of a body part and an actuator coupled with the lancing element for moving the lancing element forwardly and backwardly, wherein the actuator is adapted to drive the lancing element forwardly to a penetration speed of at most 0.7 m/s (preferably between 0.4 and 0.5 m/s) when it penetrates the skin. This allows the tip of the lancing element to be stopped under the skin with fewer vibrations and is thus associated with less pain due to the reduced speed. The reduced lancing or penetration speed also decreases the required accelerations or retardations for low puncture depths which in turn results in lower vibration excitations of all components involved in the mechanism. This increases the probability, especially in the case of mass-produced handheld devices composed of plastic parts, that the lancet is moved exactly along its lancing axis without superimposed lateral movements.

The actuator is advantageously set up such that the lancing element is accelerated until it penetrates the skin. This further reduces the instrument complexity.

Another advantageous embodiment provides that the average speed of the lancing element during the forward movement is less than 100 times the average speed of the lancing element during the return movement. This is particularly important for systems which lance as well as take up sample liquid for analysis in a one-step function. The speed ratio specified for the entire movement sequence also applies when solely considering the skin puncture. In this connection it is also advantageous when the actuator retracts the lancing element from the skin during the return movement at an average speed between 1 and 10 mm/s and in particular between 3 and 9 mm/s. The average retraction speed from the skin determines the collection period for obtaining blood at a given lancing depth. In this connection it should be sufficient for a successful collection process, when the actuator retracts the lancing element from the deepest puncture position to the skin surface during a retraction period between 200 ms and 800 ms and in particular between 250 ms and 750 ms.

In order to pierce sufficient blood capillaries and, at the same time, to damage the fewest possible nerve endings, it is advantageous when the deepest puncture position is in a range between 1 and 2 mm, and in particular at about 1.2 mm.

In order to increase the user friendliness, it is advantageous when the lancing element has a collecting structure and in particular a capillary for taking up the body fluid so that an analysis can be carried out in one process.

An additional improvement with regard to a defined puncture can be achieved by a positioning device designed to position the body part in a lancing area of the lancing element.

A suitably designed test element can be provided for detecting a constituent of the body fluid obtained using the lancing element. Such test elements can be based on an optical or electrochemical detection of a target substance.

The necessary sequence control of the lancing movement can be preferably achieved by means of the fact that the actuator has a preferably spring-driven sliding gate drive.

In order to define the limits of the lancing movement, it is advantageous when the actuator or the lancing element interacts with a stop or damping device to limit the forward movement of the lancing element.

In order to avoid transverse deflections as far as possible, at least part of the length of the lancing element should be guided in a straight line in a linear guide in the direction of movement.

In geometrically advantageous dimensions especially with regard to a low lancing pain and adequate bending rigidity, the lancing element is formed from a round wire having a diameter of less than 0.5 mm or from a flat material having a thickness of less than 0.2 mm.

With regard to the method of the invention, the object mentioned above is achieved by the following steps:
a.) providing a lancing element comprising a tip for puncturing the skin of a body part and an actuator coupled with the lancing element; and
b.) moving the lancing element forwardly by using the actuator such that the lancing element penetrates the skin to a deepest puncture position, wherein the lancing element is inserted into the skin at a penetration speed of 0.7 m/s or less (preferably at a penetration speed of between 0.4 and 0.5 m/s).

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE SEVERAL VIEWS OF THE DRAWING

The following detailed description of the embodiments of the present invention can be best understood when read in conjunction with the following drawings, where like structure is indicated with like reference numerals and in which:

FIG. 1 shows a hand-held device with an automatically driven lancing element in a diagrammatic view;

FIG. 2 shows a diagram of the speed curve of the lancing element during the forward and return movement versus distance traveled;

Figure 3:
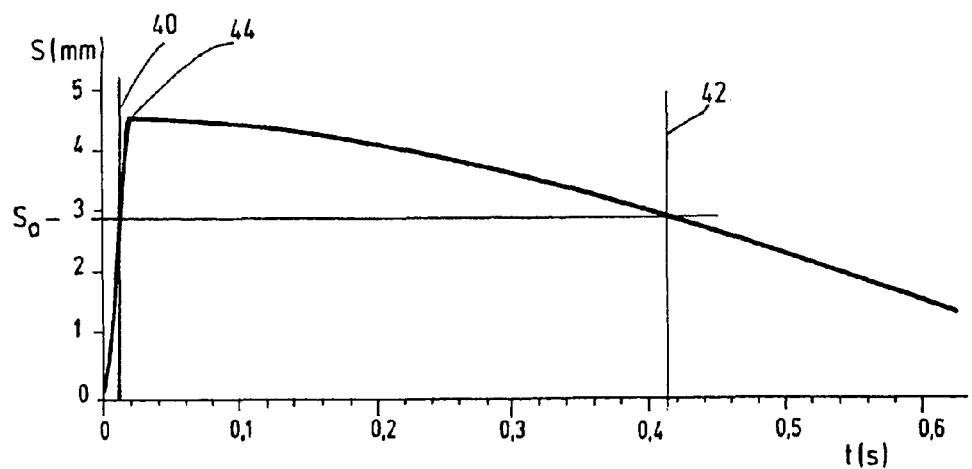
FIG. 3 shows a distance diagram of the lancing element versus time.

Skilled artisans will appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

For the purposes of describing and defining the present invention it is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

The device 10 shown in the drawing comprises an actuator 12 which drives a lancing element 14 in a forward and return movement 16, wherein the lancing element 14 can be inserted into the skin 18 of a finger 20 up to an optionally adjustable puncture position or puncture depth. Such a device can preferably be used in integrated lancing and detection systems for blood sugar measurements as part of patient self-monitoring. In this connection the actuator 12 is designed such that the penetration speed of the lancing element 14 is limited to about 0.4 to 0.5 m/s for a low-pain puncture.

As shown in FIG. 1 an opening 24 for a defined finger positioning can be provided on the device housing 22. The distal tip 26 of the lancing element 14 can be moved in the area of the opening 24 in order to obtain blood and/or tissue fluid by insertion into the skin 18. In this process the finger positioning element can promote blood flow into the puncture wound by milking the finger.

The body fluid is advantageously taken up by an optionally hydrophilically coated capillary 28 of the lancing element 14 which is fluidically connected or can be connected to an analytical test field 30. In the example shown, the lancing element 14 is formed as a disposable part from a flat sheet of stainless steel having a thickness of less than 0.2 mm. It can also be manufactured from a thin round wire. A measuring device which is not shown as such enables the detection of blood glucose for example by an optical detection of the test field 30.

In order to avoid lateral deflections, the lancing element 14 can be guided over part of its length in a linear guide 32 such that the lancing movement is carried out in a straight line that is as exact as possible. A stop or damping element that is not shown and the position of which can optionally be adjusted, enables an exact limitation at the front (distal) dead point of the lancing element movement.

The reciprocating movement 16 of the lancing element 14 can be effected by a drive control for example by means of a spring-driven rotation sliding gate drive as an actuator 12 which is known as such to a person skilled in the art for example from U.S. Pat. No. 7,223,276. In this connection a high inertia of the drive is advantageous in order to achieve the desired moderate degree of lancing dynamics even with a high elastic force.

As shown in FIG. 2, the lancing movement can be divided into three phases. In a first phase (arrow 34) the lancing element 14 is accelerated outside the skin 18. The actuator 12 preferably accelerates the lancing element 14 up to the impact position $S_0$ on the skin 18. In this manner, the maximum forward speed is achieved at the same time as when the lancing element penetrates the skin. It is also conceivable that the lancing element is already initially brought to a high forward speed and is already braked again until it impacts the skin.

In the second movement phase (arrow 36), the tip 26 of the lancing element 14 penetrates the skin 18. During this second phase, the lancing element is continually decelerated (but not necessarily linearly) until standstill where the tip 26 reaches the deepest puncture position in a range between 1 and 2 mm puncture depth, measured from the skin surface.

During the subsequent return movement (arrow 38) the lancing element 14 is pulled back out of the skin. In this connection it is important for a successful collection process that the average retraction speed is one to two orders of magnitude less than the average penetration speed. The return movement within the skin can also occur in various intervals at different speeds and with optional breaks between them. The final phase of the return movement of the lancing element after it leaves the skin at $S_0$ occurs independently of the user and can be optimized in accordance with the boundary conditions of the apparatus.

Figure 4:
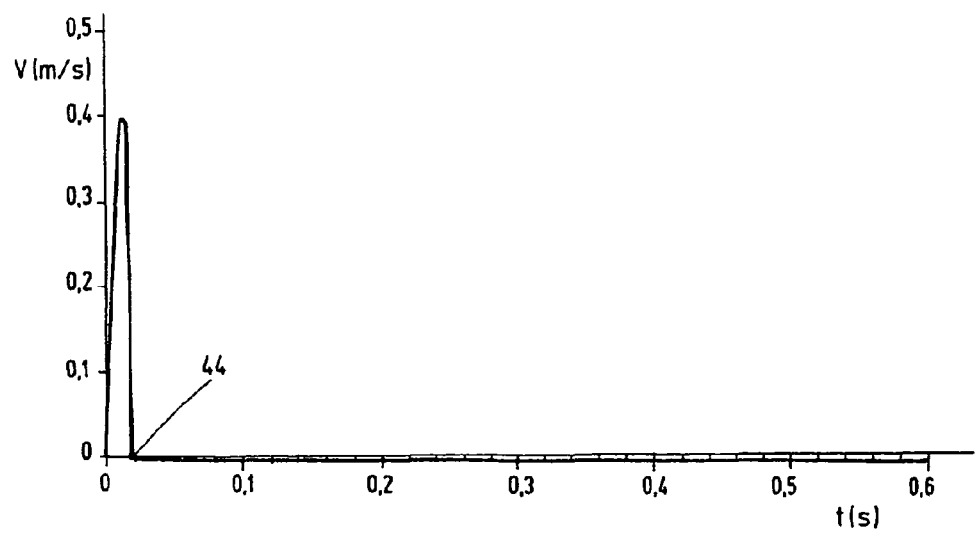
FIG. 4 shows a speed diagram of the lancing element versus time.

For further illustration the distance and speed profile of the lancing movement versus time is shown on the same scale in FIGS. 3 and 4. In FIG. 3, the horizontal line $S_0$ again marks the skin surface. The points of intercept with the distance curve marked by the vertical lines 40 and 42 thus yield the entire dwelling time of the lancing element 14 in the skin 18 of the body part 20. Whereas the forward phase until the deepest puncture position takes only a few milliseconds, a retraction time of several hundreds of milliseconds is provided from this position until it leaves the skin at position 42 to ensure an adequate filling of the capillary 28.

FIG. 4 shows the same speed time course in which the maximum of about 0.4 m/s is achieved approximately at the time of first skin contact i.e. at line 40 in FIG. 3. In general the penetration speed of the lancing element is defined as the momentary speed of the needle tip 26 in the range between the first skin contact and the deepest puncture point 44. At the deepest puncture point 44 the speed curve passes through zero, then during the return movement the average speed is at a low value between 1 and 10 mm/s.

Such time courses can be measured with a high speed camera where the time is also shown. In order to determine skin contact independently of the user, it is possible to select the reference plane defined by the device opening 24. Optionally a so-called skin dummy can also simulate the behavior of the skin. Silicon rubber with a hardness of 30 Shore-A is for example suitable for this. Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A device for obtaining a body fluid, the device comprising:
    a lancing element having a tip for puncturing skin of a body part;
    a test field fluidically connected to the lancing element; and
    an actuator coupled to the lancing element for moving the lancing element forwardly to penetrate the skin and backwardly to retract from the skin, wherein the actuator drives the lancing element forwardly at a penetration speed less than 0.7 m/s and backwardly at an average retraction speed between 0.001 and 0.01 m/s, and wherein the penetration speed is less than 100 times the average retraction speed, wherein the actuator drives the tip of the lancing element forwardly to a deepest puncture position between 1 and 2 mm below the surface of the skin, and the actuator retracts the tip of the lancing element from the deepest puncture position to the surface of the skin during a retraction period of between 200 ms and 800 ms.

2. The device of claim 1 wherein the penetration speed is 0.4 to 0.5 m/s.

3. The device of claim 1 wherein the actuator accelerates the lancing element until it penetrates the skin.

4. The device of claim 1 wherein the actuator retracts the tip of the lancing element from the deepest puncture position to the surface of the skin during a retraction period of between 250 ms and 750 ms.

5. The device of claim 1 wherein the actuator drives the tip of the lancing element forwardly to the deepest puncture position about 1.2 mm below the surface of the skin.

6. The device of claim 1 wherein the lancing element comprises a collecting structure for taking up the body fluid.

7. The device of claim 6 wherein the collecting structure comprises a capillary.

8. The device of claim 1 further comprising a positioning device that positions the body part in a lancing area of the lancing element.

9. The device of claim 1, further comprising a measuring device that detects a substance contained in the body fluid obtained with the lancing element.

10. The device of claim 1 wherein the actuator comprises a spring-driven sliding gate drive that controls the movements of the lancing element.

11. The device of claim 1 wherein at least one of the actuator and the lancing element interact with at least one of a stop or a damping device to limit movement of the lancing element.

12. The device of claim 1 further comprising a linear guide which guides at least part of the lancing element in a straight line.

13. The device of claim 1 wherein the lancing element is formed from a round wire having a diameter of less than 0.5 mm.

14. The device of claim 1 wherein the lancing element is formed from a flat material having a thickness of less than 0.2 mm.

15. A method for obtaining body fluid, comprising:
    a) providing a lancing element comprising a tip for puncturing skin of a body part and an actuator coupled with the lancing element;
    b) actuating the actuator for moving the lancing element;
    c) moving the lancing element forwardly at a penetration speed of less than 0.7 m/s to penetrate the skin to a deepest puncture position between 1 and 2 mm below the surface of the skin; and
    d) moving the lancing element backwardly to retract from the skin at an average retraction speed between 0.001 and 0.01 m/s and wherein the penetration speed is less than 100 times the average retraction speed, and the actuator retracts the tip of the lancing element from the deepest puncture position to the surface of the skin during a retraction period of between 200 ms and 800 ms.

16. The method of claim 15 wherein the actuator is used to move the lancing element forwardly and backwardly.

17. The method of claim 15 wherein the penetration speed is between 0.4 and 0.5 m/s.

18. The method of claim 17 wherein the actuator is used to move the lancing element forwardly and backwardly.

19. A device for obtaining a body fluid, the device comprising:
    a lancing element having a tip for puncturing skin of a body part;
    a test field fluidically connected to the lancing element; and
    an actuator coupled to the lancing element for moving the lancing element forwardly to penetrate the skin and backwardly to retract from the skin, wherein the actuator drives the lancing element forwardly at a penetration speed less than 0.7 m/s and backwardly at an average retraction speed between 3 and 9 mm/s, wherein the penetration speed is less than 100 times the average retraction speed.

* * * * *

UNITED STATES PATENT AND TRADEMARK OFFICE
CERTIFICATE OF CORRECTION

PATENT NO. : 8,608,667 B2  
APPLICATION NO. : 12/174346  
DATED : December 17, 2013  
INVENTOR(S) : Hoerauf et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 368 days.

Signed and Sealed this
Twelfth Day of May, 2015

Michelle K. Lee
*Director of the United States Patent and Trademark Office*